(12) United States Patent
Henry et al.

(10) Patent No.: US 6,436,425 B1
(45) Date of Patent: *Aug. 20, 2002

(54) METHOD AND NON-GELLING COMPOSITION FOR INHIBITING POST-SURGICAL ADHESIONS

(75) Inventors: Raymond L. Henry, St. Clair Shores; Lorraine E. Reeve, Dexter, both of MI (US); Stephen G. Flore, San Diego, CA (US); Frederick J. Foley, Bedford, NH (US)

(73) Assignee: MDV Technologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/499,887

(22) Filed: Feb. 8, 2000

Related U.S. Application Data

(60) Continuation of application No. 09/059,716, filed on Apr. 13, 1998, now abandoned, and a continuation-in-part of application No. 08/954,630, filed on Oct. 20, 1997, now abandoned, which is a continuation of application No. 08/599,116, filed on Feb. 9, 1996, now Pat. No. 5,681,576, said application No. 09/059,716, is a continuation of application No. 08/540,287, filed on Oct. 6, 1995, now abandoned, and a continuation of application No. 08/208,418, filed on Mar. 8, 1994, now abandoned, which is a continuation of application No. 07/977,483, filed on Nov. 17, 1992, now Pat. No. 5,366,735, which is a division of application No. 07/517,283, filed on May 1, 1990, now abandoned, which is a continuation-in-part of application No. 07/449,215, filed on Dec. 12, 1989, now Pat. No. 5,135,751, which is a division of application No. 07/272,199, filed on Nov. 16, 1988, now Pat. No. 4,911,926.

(51) Int. Cl.$^7$ .......................... A61P 41/00; A61K 47/34

(52) U.S. Cl. .................. 424/423; 424/78.37; 514/772.7

(58) Field of Search .............................. 424/78.03, 423, 424/78.37; 514/944, 772.7

(56) References Cited

U.S. PATENT DOCUMENTS

| | | | |
|---|---|---|---|
| 2,674,619 A | 4/1954 | Lundsted | 260/485 |
| 2,677,700 A | 5/1954 | Jackson et al. | 260/488 |
| 2,979,528 A | 4/1961 | Lundsted | 260/584 |
| 3,036,118 A | 5/1962 | Jackson et al. | 260/484 |
| 3,535,307 A | 10/1970 | Moss et al. | 260/209 |
| 3,590,125 A | 6/1971 | Hymes | 424/78 |
| 3,639,575 A | 2/1972 | Schmolka | 424/78 |
| 3,640,741 A | 2/1972 | Etes | 106/170 |
| 3,641,240 A | 2/1972 | Hymes et al. | 424/78 |
| 3,740,421 A | 6/1973 | Schmolka | 424/65 |

(List continued on next page.)

FOREIGN PATENT DOCUMENTS

| | | |
|---|---|---|
| EP | 0103290 A2 | 3/1984 |
| EP | 0274431 A2 | 7/1988 |
| EP | 0386960 A2 | 2/1990 |
| EP | 0369764 | 5/1990 |

(List continued on next page.)

OTHER PUBLICATIONS

Ellis, H. The Cause and Prevention of PostOperative Intraperitoneal Adhesions, Surgery, Gynecology, & Obstetrics 133: pp. 497–511 (1971).

Linsky et al., Adhesion Reduction in the Rabbit Uterine Horn Model Using an Absorbable Barrier, TC–7 J. of Reproductive Medicine 32 (1): pp. 17–20 (1987).

(List continued on next page.)

Primary Examiner—Edward J. Webman

(57) ABSTRACT

Non-gelling polyoxyalkylene compositions, and methods of their use for inhibiting surgical adhesion formation/reformation in mammals are disclosed. The useful non-gelling compositions preferably comprise polyoxyalkylene block copolymer at desired concentrations with or without a therapeutic agent. When used with an incorporated drug, the non-gelling compositions serve as a carrier providing sustained or prolonged release of the therapeutic agent.

8 Claims, 5 Drawing Sheets

U.S. PATENT DOCUMENTS

| | | | |
|---|---|---|---|
| 3,829,506 A | 8/1974 | Schmolka et al. | 260/615 |
| 3,847,155 A | 11/1974 | Bernaola | 128/334 |
| 3,867,521 A | 2/1975 | Miskel et al. | 424/37 |
| 3,867,533 A | 2/1975 | Schmolka | 424/258 |
| 3,947,250 A | 3/1976 | Pollack | 23/230 |
| 4,043,344 A | 8/1977 | Landi et al. | 128/335.3 |
| 4,047,533 A | 9/1977 | Periaccante et al. | 128/335.5 |
| 4,076,799 A | 2/1978 | Willer et al. | 424/45 |
| 4,100,271 A | 7/1978 | Krezanoski | 424/78 |
| 4,125,608 A | 11/1978 | Blum et al. | 424/180 |
| 4,188,373 A | 2/1980 | Krezanoski | 424/78 |
| 4,360,451 A | 11/1982 | Schmolka | 252/316 |
| 4,368,185 A | 1/1983 | Mizuno et al. | 424/78 |
| 4,439,196 A | 3/1984 | Higuchi | 604/890 |
| 4,465,663 A | 8/1984 | Schmolka | 424/62 |
| 4,474,751 A | 10/1984 | Haslam et al. | 424/78 |
| 4,474,752 A | 10/1984 | Haslam et al. | 424/78 |
| 4,474,753 A | 10/1984 | Haslam et al. | 424/78 |
| 4,478,822 A | 10/1984 | Haslam et al. | 424/78 |
| 4,495,168 A | 1/1985 | Schmolka | 424/45 |
| 4,495,169 A | 1/1985 | Schmolka | 424/47 |
| 4,511,563 A | 4/1985 | Schmolka | 514/162 |
| 4,540,407 A | 9/1985 | Dunn | 604/292 |
| 4,651,736 A | 3/1987 | Sanders | 128/305 |
| 4,767,619 A | 8/1988 | Murray | 424/78 |
| 4,795,642 A | 1/1989 | Cohen et al. | 424/455 |
| 4,810,503 A | 3/1989 | Carson et al. | 424/76.3 |
| 4,861,760 A | 8/1989 | Mazuel et al. | 514/54 |
| 4,879,062 A | 11/1989 | Moore | 252/315.1 |
| 4,879,109 A | 11/1989 | Hunter | 424/83 |
| 4,883,660 A | 11/1989 | Blackman et al. | 424/78 |
| 4,889,722 A | 12/1989 | Sheffield et al. | 424/450 |
| 4,895,724 A | 1/1990 | Cardinal et al. | 424/418 |
| 4,911,926 A | 3/1990 | Henry et al. | 424/426 |
| 4,917,886 A | 4/1990 | Asche et al. | 424/81 |
| 5,068,225 A | 11/1991 | Pennell et al. | 514/57 |
| 5,071,644 A | 12/1991 | Viegas et al. | 514/772.7 |
| 5,077,033 A | 12/1991 | Viegas et al. | 514/668 |
| 5,124,151 A | 6/1992 | Viegas et al. | 424/422 |
| 5,126,141 A | 6/1992 | Henry | 424/423 |
| 5,135,751 A | 8/1992 | Henry et al. | 424/426 |
| 5,143,731 A | 9/1992 | Viegas et al. | 424/486 |
| 5,366,735 A | 11/1994 | Henry | 424/426 |
| 5,369,131 A | 11/1994 | Poli et al. | |
| 5,484,610 A | 1/1996 | Bae | |

FOREIGN PATENT DOCUMENTS

| | | |
|---|---|---|
| EP | 0126684 B1 | 8/1991 |
| EP | 0455396 A1 | 11/1991 |
| EP | 0517160 B1 | 2/1992 |
| EP | 0227494 B1 | 4/1992 |
| EP | 0551626 A1 | 7/1993 |
| EP | 0598116 A1 | 5/1994 |
| EP | 0640342 | 3/1995 |
| EP | 0694310 A1 | 1/1996 |
| WO | 9004971 | 5/1990 |
| WO | 9403157 | 2/1994 |
| WO | 9414415 | 7/1994 |
| WO | 9509626 | 4/1995 |
| WO | 9524430 | 9/1995 |
| WO | 9620696 | 7/1996 |

OTHER PUBLICATIONS

Schmolka I.R., Artificial Skin I Preparation and Properties of Pluronic F–127 Gels for Treatment of Burns, J. of Biomed. Mat. Res. 6: pp. 571–582 (1972).

Smith et al., Pluronic F–68 Reduces the Endothelial Adherence and Improves the Rheology of Liganded Sickle Erythrocytes, Blood 69(6): pp. 1631–1636 (1987).

Hunter et al. The Adjuvant Activity of Nonionic Block Polymers Surfactants J. of Immunology 127(3): pp. 1244–1250 (1981).

Edlich et al., The Molecular Basis for Toxicity of Surfactants in Surgical Wounds, J. of Surgical Res. 14(4): pp. 277–284 (1973).

Menzies et al., Intestinal Obstruction From Adhesions—How Big is the Problem, Annals of the Royal College of Surgeons of England 72(1): pp. 60–63 (1990).

Borten, et al. Recurrent Anaphylactic Reaction to Intraperitoneal Dextran 75 Used For Prevention of Postsurgical Adhesions Obstetrics & Gynecology 61(6): pp. 755–757 (1983).

Holtz et al., Inhibition of Peritoneal Adhesion Re–Formation After Lysis With Thirty–Two Per Cent Dextran 70, Fertility and Sterility 34(4): pp. 394–395 (1980).

Holtz et al., Effect of Thirty–Two Per Cent Dextran 70 On Peritoneal Adhesion Formation and Re–Formation After Lysis, Fertility and Sterility 33(6): pp. 660–662 (1980).

Shimanuki et al., Localized Prevention of Postsurgical Adhesion Formation and Reformation With Oxidized Regenerated Cellulose, J. Biomed. Mat. Res. 21: pp. 173–185 (1987).

Steinleitner et al., New Modalities Under Development For Adhesion Prevention: Immunomodulatory Agents and Poloxamer Barrier Materials, Gynecologic Surgery and Adhesion Prevention pp. 235–251 (eds. Wiley–Liss, Inc. 1993).

Steinleitner et al., Poloxamer 407 as an Intraperitoneal Barrier Material For The Prevention of Postsurgical Adhesion Formation and Reformation in Rodent Models for Reproductive Surgery, Obstetrics & Gynecology 77(1): pp. 48–52 (1991).

DiZerega et al., Reduction of Post–Operative Pelvic Adhesions with Intraperitoneal 32% Dextran 70: A Prospective, Randomized Clinical Trial, Fertility and Sterility 40(5): pp. 612–619 (1983).

Caspi et al., The Importance of Periadnexal Adhesions in Tubal Reconstructive Surgery For Infertility, Fertility and Sterility 31(3): pp. 296–300 (1979).

Oelsner et al., Chondroitin Sulphate: A New Intraperitoneal Treatment for Postoperative Adhesion Prevention in the Rabbit J. of Reproductive Medicine 32(11): pp. 812–814 (1987).

Peterson et al., Effect of Various Methods of Restoring Flexor Sheath Integrity on the Formation of Adhesions After Tendon Injury J. of Hand Surgery 15A(1): pp. 48–56 (1990).

Kim et al., Pluronic® Polyol: A Potential Alloplastic Keratorefractive Material J. of Cataract Refractive Surgery 14: pp. 312–316 (1988).

Musich et al., Infertility Laparoscopy in Perspective: Review of 500 Cases, The Amer. J. of Obstetrics & Gynecology 143(3): pp. 293–303 (1982).

Punnonen, R. et al., Polyethylene Glycol 4000 in the Prevention of Peritoneal Adhesions, 38(4) Fertility and Sterility pp. 491–492 (Oct. 1982).

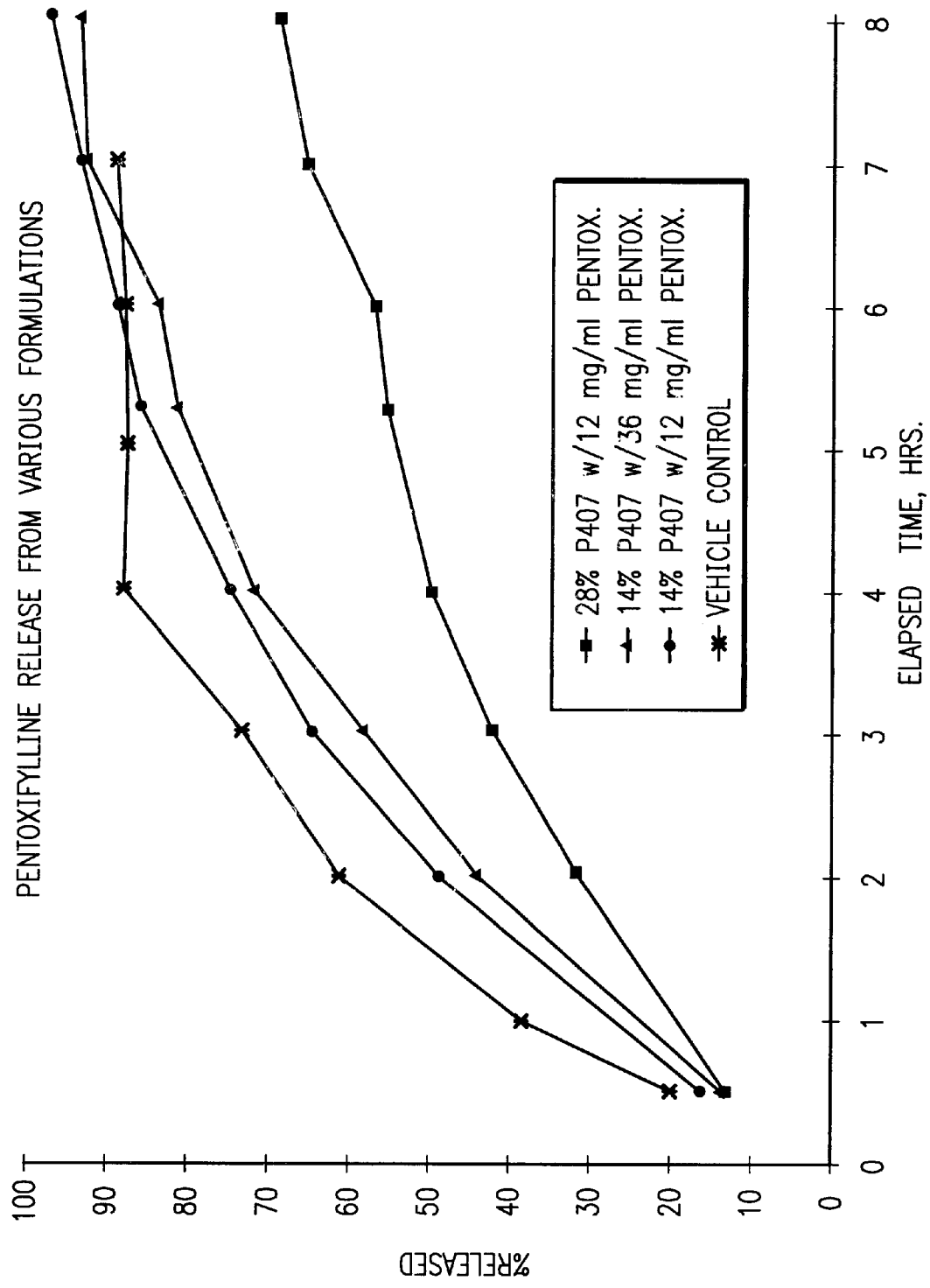

METHOD AND NON-GELLING COMPOSITION FOR INHIBITING POST-SURGICAL ADHESIONS

This application is a continuation of Ser. No. 09/059,716 Apr. 13, 1998 abandoned Which is a continuation of Ser. No. 08/540,287 Oct. 6, 1995 abandoned and a CIP of Ser. No. 08/954,630 Oct. 20, 1997 abandoned which is a continuation of Ser. No. 08/599,116 Feb. 9, 1996 U.S. Pat. No. 5,681,576 and a continuation of Ser. No. 08/208,418 Mar. 8, 1994 abandoned which is a continuation of Ser. No. 07/977,483 Nov. 17, 1992 U.S. Pat. No. 5,366,735 which is a DIV of Ser. No. 07/517,283 May 1, 1990 abandoned which is a CIP of Ser. No. 07/449,215 Dec. 12, 1989 U.S. Pat. No. 5,135,751 which is a DIV of Ser. No. 07/272,199 Nov. 16, 1988 U.S. Pat. No. 4,911,926.

BACKGROUND OF THE INVENTION

1. Field of the Invention

This invention relates to methods and compositions for inhibiting adhesions in the mammalian abdominal or thoracic cavity or other body spaces, whether accidentally or surgically created.

2. Description of the Prior Art

There is a need for improved methods and compositions for inhibiting adhesion formation/reformation in body spaces of mammals, whether accidentally or surgically created. According to Ellis in a review entitled, "The Cause And Prevention of Post-operative Intraperitoneal Adhesions," in *Surgery Gynecology and Obstetrics* for September 1971, volume 133, pages 497–509, at pages 502–503, the prevention of adhesions has been the subject of an enormous amount of work since the beginning of this century. According to Ellis, these attempts have included means of preventing the fibrin-coated walls of the intestine from reaching each other by distending the abdomen with oxygen or filling the abdomen with saline solution, paraffin, olive oil, lanolin, concentrated dextrose solution, macromolecular solutions of all sorts, and silicones.

Menzies and Ellis in a review entitled, "Intestinal Obstruction from Adhesions—How Big is the Problem?" *Annals of the Royal College of Surgeons of England*, vol 72 pages 60–63, 1990 reported finding adhesions in 10.4% of 115 patients with first-time laparotomies while 93% of 210 patients had intra-abdominal adhesions due to previous surgery. Admission for intestinal obstruction was made for 0.9% of 28,297 general surgery patients while 3.3% of 4,502 laparotomy patients were admitted for intestinal obstruction due to adhesions. These data emphasize the magnitude of readhesions after adhesiolysis or from subsequent surgical procedures. The authors state on p. 62, that there is currently no effective treatment that prevents their recurrence.

High molecular weight dextran either alone or in combination with dextrose has been used in the prevention of peritoneal adhesions subsequent to surgery. Dextran is clinically standardized to a low molecular weight of about 75,000 by partial hydrolysis and fractional precipitation of the high molecular weight particles which normally have molecular weights up to 200,000. Dextran is a polymer of glucose which has a chain-like structure and is produced from sucrose by Lenconostoc bacteria. In articles appearing in *Fertility and Sterility*, volume 33, number 6, June 1980, pages 660–662, Holtz, Baker, and Tsai and volume 34, number 4, October, 1980, pages 394–395, by Holtz and Baker, results are reported of the adhesion reducing effects of a 32% (aqueous) solution of Dextran 70 containing 10% dextrose (sold under the trade name HYSKON by Pharmacia, of Piscataway, N.J.). Holtz et al postulate several mechanisms of action in the prevention of peritoneal adhesions utilizing HYSKON® including a simple mechanical separation of adjacent surfaces, termed a hydroflotation effect.

Project coordinator diZerega and several contributors have reported the results of a large study in an article entitled, "Reduction of Post-operative Pelvic Adhesions with Intraperitoneal 32% Dextran 70: A Prospective, Randomized Clinical Trial," in *Fertility and Sterility*, volume 40, number 5, for November 1983, pages 612–619. The authors, on page 618, indicate that the use of Dextran intraperitoneally has limitations such as the reported tendency of HYSKON to support bacterial proliferation and concern over the anaphylactoid potential of dextran. In addition, the benefit of Dextran 70 in preventing post-operative adhesions was shown to be limited to the more lower regions of the pelvis.

Borten, Seibert, and Taymor in *Obsterics and Gynecology*, vol 61, number 6, June, 1983, pages 755–757 report in an article entitled, "Recurrent Anaphylactic Reaction to Intraperitoneal Dextran 75 Used for Prevention of Postsurgical Adhesions". These authors indicate that anaphylactic reaction to Dextran administered intravenously is well documented and report such a reaction after intraperitoneal administration of Dextran.

The use of ethylene oxide/propylene oxide block copolymers as surfactants in surgical scrub solutions and the topical application of 10% solutions of these copolymers to wounds is described in Edlich et al in the *Journal of Surgical Research*, volume 14, number 4, April 1973, pages 277–284. The test results indicate that copolymers having an ethylene oxide:propylene oxide ratio of 4:1 provide less inflammatory response in a wound to which the copolymer is applied in comparison with a copolymer having an ethylene oxide:propylene oxide ratio of 1:4. There is no indication by Edlich et al or any cited prior art that such copolymers are useful in reducing post-operative adhesions or that isotonic, aqueous solutions of such copolymers are useful in reducing post-operative adhesions.

Over the years, methods have been developed to achieve the efficient delivery of a therapeutic drug to a mammalian body part requiring pharmaceutical treatment. Use of an aqueous composition which can be applied at room temperature as a liquid but which forms a semi solid gel when warmed to body temperature has been utilized as a vehicle for drug delivery. Such a system combines ease of application with greater retention at the site requiring treatment than would be the case if the aqueous composition were not converted to a gel as it is warmed to mammalian body temperature. In U.S. Pat. No. 4,188,373, PLURONIC® polyols are used in aqueous compositions to provide thermally gelling aqueous systems. Adjusting the concentration of the polymer, provides the desired sol-gel transition, that is, the lower the concentration of polymer, the higher the sol-gel transition temperature.

In U.S. Pat. Nos. 4,474,751; 752; 753; and 4,478,822, drug delivery systems are described which utilize thermosetting polyoxyalkylene gels; the unique feature of these systems is that both the gel transition temperature and/or the rigidity of the gel can be modified by adjustment of the ionic strength, as well as by the concentration of the polymer.

Other patents disclosing pharmaceutical compositions which rely upon an aqueous gel composition as a vehicle for the application of the drug or cosmetic preparation are U.S. Pat. Nos. 4,883,660; 4,861,760; 4,810,503; 4,767,619; and 4,511,563.

Steinleitner et al in an article entitled, "Poloxamer 407 as an Intraperitoneal Barrier Material for the Prevention of Post-Surgical Adhesion Formation and Reformation in Rodent Models for Reproductive Surgery, *Obstetrics and Gynecology*, volume 1, pages 48–52, 1991, discloses the anti-adhesion properties of poloxamer 407. Polxamer 407 is a biocompatable polymer, the viscosity of which is dependent upon temperature and concentration in aqueous solutions. The material is a liquid at room temperature and is a solid at body temperature. In one experiment, poloxamer solutions and concentrations ranging from 15–35% were applied to the lesions on the uterine horn of hamsters. Significant reduction in post-traumatic adhesion formation was observed following treatment with the poloxamer solutions. In a second experiment, the polymer was used in a paradigm for a typical situation encountered in fertility surgery, that is, the prevention of adhesion reformation after lysis of established adhesions. The effects of applying poloxamer 407 after adhesiotomy in rabbits was compared to controls that had received no treatment. The adhesion reformation was reduced by a poloxamer 407 treatment.

Steinleitner in an article entitled, "New Modalities Under Development for Adhesion Prevention; "Immunomodulatory Agents and Poloxamer Barrier Materials", *Gynecologic Surgery and Adhesion Prevention*, pages 235–251, 1993 discloses a review of the pathophysiology of peritoneal wound repair that summarizes studies evaluating immunomodulatory agents designed to favorably influence aspects of post surgical healing. Besides describing the physiology of peritoneal repairs, the authors of the studies list a number of immunomodulatory agents used in adhesion prevention such as calcium channel blocking agents and other agents such as pentoxifylline. The authors emphasize the application of barrier materials to effect physical separation of injured viscera stating that it may be the most effective therapy currently available to surgeons. The ideal barrier material should be biocompatible, be absorbable and have a neutral or beneficial effect on the events of peritoneal healing. Further, the barrier material should serve as a local delivery system for pharmacologic anti-adhesion treatments. Poloxamer 407 has been identified as particularly well suited for use in preventing adhesion formation or reformation as a barrier material in infertility surgery.

The Steinleitner review discloses the use of pentoxifylline in preventing the formation of post surgical adhesions. Pentoxifylline is a methylxanthine derivative which improves the flow properties of blood by decreasing its viscosity. In patients with chronic peripheral arterial disease, pentoxifylline increases blood flow to the affected microcirculation and enhances tissue oxygenation. Steinleitner et al. used the hamster uterine horn primary injury model and administered doses of 0.1 to 10 mg\kg subcutaneously at 12 hour intervals. This regimen was found to provide protection against post-traumatic adhesion formation.

While the prior art discloses the use of pentoxifylline and poloxamer 407 separately as agents that may be useful in inhibiting or reducing the formation/reformation of adhesions in the peritoneal cavity for mammals, there is a need for an improved non-gelling composition that can be applied directly to the body cavity and a process for reducing post surgical adhesion formation/reformation.

SUMMARY OF THE INVENTION

Non-gelling polyoxyalkylene compositions, therapeutic agents, and a method are disclosed for inhibiting post surgical adhesion formation/reformation in mammals following injury to the organs of a body cavity. The compositions of the invention are also useful in reducing adhesion formation/reformation in body cavities. The useful compositions comprise a surfactant and a non-gelling polyoxyalkylene block copolymer at desired concentrations with or without a therapeutic agent. The non-gelling polyakylene block copolymer serves as a carrier with a sustained or prolonged release of the therapeutic agent.

Single phase systems are also useful and may contain aqueous solutes, aqueous solvents, and other aqueous additives. Homogeneous, single phase systems can contain such additives as alginate, cellulosics, polysaccharides, glycerol, polyethers, and collagen altering the functionality of the system. The concentration of the block copolymer in the compositions of the present invention to take advantage of the non-gelation properties of certain polyoxyalkylene block copolymers. Typically, formulations of the present invention may contain up to about 16% (w/w) of the polyoxyalkylene block copolymer of the present invention.

The aqueous solutions of block copolymers can be provided as isomotically and pH balanced compositions which match the pH and osmotic pressure of mammalian bodily fluids. Subsequent to deposition of the compositions of the invention on the tissues of the peritoneal, pelvic, or pleural cavity of a mammal, or other body spaces, the polyxyalkylene block copolymer is absorbed into the circulatory system and is eventually excreted, mainly in the urine. In addition to functioning as a means of reducing post-operative adhesion formation/reformation in mammals following surgical or accidental injury or inflammation to the peritoneal, pelvic or pleural cavity or other body spaces, a therapeutic agent and polyoxyalkylene compositions provide an osmotically balanced environment surrounding the surgical injury which reduces adhesion formation/reformation. For instance, the polyoxyalkylene block copolymer and therapeutic agent can be instilled within the uterine cavity as a distending medium during diagnostic or operative intrauterine endoscopic procedures. This procedure has two advantages. First, since certain aqueous concentrations of the preferred polyoxyalkylene block copolymers form a clear gel, their use is well suited for visualization of the tissues within the uterine cavity. Second, since these aqueous solutions are liquids at room temperature and below and form a clear gel at body temperature, the use of said solutions to separate the uterine cavity walls will diminish or prevent post-surgical adhesion formation. Similarly, the application of the aqueous, polyxyalkylene, capped polyether-surfactant pentoxifylline combination as gels provide a similar adhesion reducing effect.

DESCRIPTION OF THE DRAWINGS

FIG. 5 illustrates pentoxifylline release from formulations of 28% poloxamer 407 with 12 mg/ml pentoxifylline, 14% poloxamer 407 with 36 mg/ml pentoxifylline and 14% poloxamer 407 with 12 mg/ml penoxifylline.

DETAILED DESCRIPTION OF THE INVENTION

Figure 1:
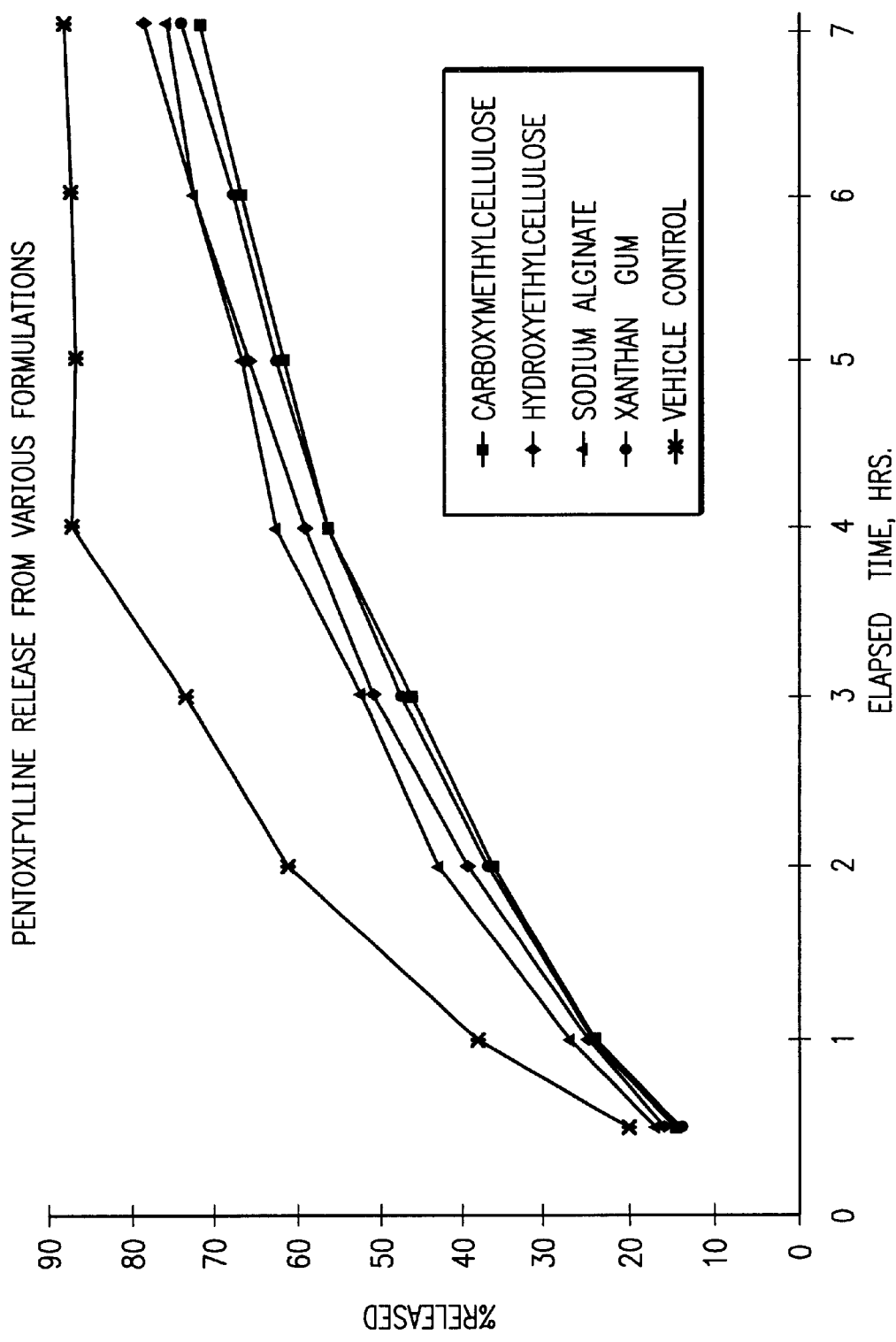
FIG. 1 is a chromogram of a poloxamer 407 analysis by gel permeation choromography.

A process and composition are disclosed for inhibiting post-operative adhesion formation/reformation in mammals following surgical or accidental injury or inflammation to the organs of the peritoneal or pleural cavity or other body spaces. Patent application Ser. No. 08/954,630 filed Oct. 20, 1997 is hereby incorporated by reference. In this specification and claims, the terms "peritoneal" and "abdominal" cavity are used as synonyms, as are the terms "pleural" and "thoracic" cavity. By the term "body spaces", we mean cavities or areas of the body where there is an environment for allowing the composition of the present invention to be in contact with body tissues. "Body spaces" may be further defined as peritoneal, abdominal, and thoracic cavities as well as joints and areas of the body containing synovial fluid. The compositions include pentoxifylline, which is a methylxanthine derivative, and indicated for the treatment of patients with intermittent claudication on the basis of chronic occlusive arterial disease of the limbs.

The present invention discloses a novel use for pentoxifylline, in effective amounts, in combination with the polyoxyalkylene compositions disclosed herein, by providing for the inhibition of post surgical adhesion formation/reformation when applied directly onto a body tissue following injury.

In one embodiment of the invention, the preferred aqueous, polyoxyalkylene block copolymer compositions are prepared at a pH and osmotic pressure which match that of bodily fluids (pH 7.4 and 290 mOsm/kg). When certain of the polyoxyalkylene block copolymers of the invention are present in aqueous solutions at concentrations preferably of about 1% to about 16%, preferably about 7 to about 14% by weight such compositions.

Alternatively, useful compositions of the invention include aqueous compositions comprising at least one polyoxyalkylene block copolymer which do not form gels at mammalian body temperature as well as aqueous, isotonic, polyoxyalkylene gel polymers comprising an alpha olefin epoxide capped polyether and a surfactant. It is believed that the aqueous compositions of the invention which do not form gels upon contact with living mammalian tissue as well as those which are applied to mammalian tissue in the gel state, also function to prevent the formation/reformation of adhesions subsequent to surgical procedures incurred by a mechanism of action which has been termed in the prior art "hydroflotation". Thus the injured tissues are prevented from contacting adjacent tissues by the means of the inclusion of a foreign fluid or gel in the peritoneal, pelvic, or pleural cavity or other body spaces. It is believed that the mechanism of action to prevent the formation/reformation of adhesions is, in addition to hydroflotation, properly characterized as the result of separating the adjacent mammalian tissues by an adherent coating.

The polyoxyalkylene block copolymer compositions of one embodiment of the invention include at least one block copolymer as defined below, in combination with pentoxifylline. The copolymer is applied to injured tissue in combination with pentoxifylline, both in effective amounts. The block copolymer compositions of the invention comprise at least one polyoxyalkylene block copolymer of the formula:

$$Y[(A_n\text{—}E\text{—}H)]_x \quad (I)$$

wherein A is a polyoxyalkylene moiety having an oxygen/carbon atom ration of less than 0.5, x is at least 1, Y is derived from water or an organic compound containing x reactive hydrogen atoms, E is a polyoxyalkylene moiety constituting at least about 60% by weight of the copolymer, n has a value such that the average molecular weight of A is at least about 500 to about 900, as determined by the hydroxyl number of a hydrophobe base intermediate:

$$Y[(A_n\text{—}H)]_x \quad (II)$$

and the total average molecular weight of the copolymer is at least about 5000.

In addition to those polyoxyalkylene polymers described above, which are suitable in combination with effective amounts of pentoxifylline in the formation of the compositions of the invention, other polyoxyalkylene polymers which form gels at low concentrations in water are suitable. These are described in U.S. Pat. No. 4,810,503, incorporated herein by reference. These polymers are prepared by capping conventional polyoxyalkylene polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant which generally do not exceed 10% by weight total. Detailed methods of preparing these aqueous gels are disclosed in U.S. Pat. No. 4,810,503. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers of this invention. Ethylene oxide homopolymers capped with said alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably, from 80° C. to 130° C., under an inert gas pressure, preferably, from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide. The ethylene oxide and the alkylene oxides having from 3 to 4 carbon atoms are used in said intermediates in amounts so that the resulting polyether product will contain at least 10 percent by weight, preferably about 60 percent to about 80 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers of the invention.

Since the preparation of heteric and block copolymers of alkylene oxides and ethylene oxide homopolymers are well known in the art, further description of the preparation of said polymers is unnecessary. Further details of the preparation of heteric copolymers of lower alkylene oxides can be obtained in U.S. Pat. No. 3,829,506, incorporated herein by reference. Further information on the preparation of block copolymers of lower alkylene oxides can be obtained in U.S. Pat. Nos. 3,535,307; 3,036,118; 2,979,578; 2,677,700; and 2,675,619 incorporated herein by reference.

The surfactants may be ionic or non-ionic and many surfactants and types of surfactants may be employed. While all surfactants may not be effective in the preparation of osmotically balanced gels of the instant invention, the fact that many are effective makes it a simple matter for one skilled in the art to select such surfactant with a minimum of trial and error.

The amounts of capped polyether polymer and surfactant may be as little as 1.0 percent by weight or less of each depending on the type and amount of the other components. There appears to be no maximum amount of either component than that dictated by the solubility and osmolality in an aqueous solution. However, the total amount of capped polymer and surfactant would generally not exceed 10 percent by weight.

Preferably, the block copolymers which are useful are selected from those defined above in formula I which contain at least about 60% by weight, preferably at least about 70%, by weight of the residue of ethylene oxide (polyoxyethylene moiety). Said copolymers have a total average molecular weight of at least about 5000, and form a gel at mammalian body temperature, when in an aqueous solution at a concentration generally, of about 10 to about 40%, and preferably, about 15 to about 30% by weight.

The proportion of water used is about 60% to about 90%, by weight, preferably, about 70% to about 85%, by weight based upon the total weight of the composition of the invention. Useful polyoxyalkylene block copolymers which will form gels in such aqueous solutions can be prepared using a hydrophobe base (such as A in Formulas I and II) derived from propylene oxide, butylene oxide, or mixtures thereof. These block copolymers and representative methods of preparation are further generally described in U.S. Pat. Nos. 2,677,700; 2,674,619; and 2,979,528, incorporated herein by reference.

Generally, the polyoxybutylene-based block copolymers useful in the compositions of the invention are prepared by first condensing 1,2 butylene oxide with a water soluble organic compound initiator containing 1 to about 6 carbon atoms such as 1,4 butylene glycol or propylene glycol and at least 2 reactive hydrogen atoms to prepare a polyoxyalkylene polymer hydrophobe of at least about 500, preferably at least about 1000, most preferably at least about 1500 average molecular weight. Subsequently, the hydrophobe is capped with an ethylene oxide residue. Specific methods for preparing these compounds are described in U.S. Pat. No. 2,828,345 and British Patent No. 722,746, both of which are hereby incorporated by reference.

Useful polyoxybutylene based block copolymers conform to the following generic formula:

$$HO(C_2H_4O)_b(C_4H_8O)_a(C_2H_4O)_bH \qquad (III)$$

wherein a is an integer such that the hydrophobe base represented by $(C_4H_8O)_a$ has a molecular weight of at least about 500, preferably at least about 1000 and most preferably at least about 3000, as determined by hydroxyl number, the polyoxyethylene chain constituting at least about 60%, preferably at least about 70% by weight of the copolymer, and the copolymer having a total average molecular weight of at least about 5000, preferably at least about 10,000, and, most preferably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base polymer.

Polyoxyethylene-polyoxypropylene block copolymers which can be used to form aqueous gels can be represented by the following formula:

$$HO(C_2H_4O)_b(C_3H_6O)_a(C_2H_4O)_bH \qquad (IV)$$

wherein a is an integer such that the hydrophobe base represented by $(C_3H_6O)$ has a molecular weight of at least about 900, preferably at least about 2500 average molecular weight, as determined by hydroxyl number; the polyoxyethylene chain constituting at least about 60%, preferably at least about 70% by weight of the copolymer, and the copolymer having a total average molecular weight of at least about 5000, preferably at least about 10,000.

Polyoxyethylene-polyoxypropylene block copolymer adducts of ethylenediamine which can be used may be represented by the following formula:

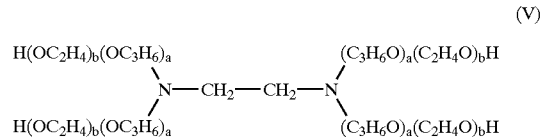

(V)

wherein a and b are integers such that the copolymer may have (1) a hydrophobe base molecular weight of at least about 2000, preferably at least about 3000, and most preferably at least about 4500, (2) a hydrophile content of at least about 60%, preferably at least about 70% by weight, and (3) a total average molecular weight of at least about 5000, preferably at least about 10,000, and most preferably at least about 15,000.

The hydrophobe base of the copolymer of formula V is prepared by adding propylene oxide for reaction at the site of the four reactive hydrogen atoms on the amine groups of ethylenediamine. An ethylene oxide residue is used to cap the hydrophobe base. These hydrophile polyoxyethylene groups are controlled so as to constitute about 60% to about 80% by weight of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° C. to about 10° C. in water.

The organic compound initiator which is utilized in the process for the preparation of the polyoxyalkylene block copolymers generally is water or an organic compound and can contain a plurality of reactive hydrogen atoms. Preferably, Y in formulas I and II above is defined as derived from a water soluble organic compound having 1 to about 6 carbon atoms and containing x reactive hydrogen atoms where x has a value generally, of at least 1, preferably, a value of at least 2. Y is derived from water soluble organic compounds having at least two reactive hydrogen atoms. Falling within the scope of the compounds of the present invention are water soluble organic compounds such as propylene glycol, glycerin, pentaerythritol, trimethylolpropane, ethylenediamine, and mixtures thereof and the like.

The physical form of the polyoxyalkylene block copolymers can be a viscous liquid, a paste, or a solid granular material depending upon the molecular weight of the polymer. Useful polyoxyalkylene block copolymers generally have a total average molecular weight of about 5000 to about 50,000, preferably about 5,000 to about 35,000 and most preferably about 5,000 to about 15,000.

Preferably the polyoxyalkylene block copolymer is applied to surgically injured tissue as an aqueous solution which upon contact with living mammalian tissue forms an adherent coating. Where a polyoxyalkylene block copolymer is a viscous liquid or paste, the compositions can be applied without dilution to areas of surgical injury in the abdominal or thoracic cavities. The aqueous solution or viscous liquid or paste may be applied to form an adherent coating on the body tissues in the body cavity to aid in the inhibition of the formation or reformation of adhesions. Serving as a barrier, the composition of the present invention prevents the close proximity or contact of tissues between surfaces of which adhesions would form.

Another function of the non-gelling composition is to deliver drugs to the site of treatment. In a preferred embodiment of the invention, the non-gelling composition is used to deliver pentoxifylline to the site of treatment. The amount of pentoxifylline used is an amount effective to inhibit adhesion formation/reformation in combination with the block copolymers of this invention when applied as a liquid or gel to a body cavity following surgery. Typically, the amount may be about 0.05% to about 5.0% by weight, preferably about 0.1% to about 2.0% by weight, based upon the total weight of the compositions of the invention.

The poloxamers are a series of copolymers composed of two polyoxyethylene blocks separated by a polyoxypropylene block. (Lundsted, L. G., U.S. Pat. No. 2,674,619, 1954; Schmolka, I. R. "Poloxamers in the Pharmaceutical Indusdtry", in *Polymers for Controlled Drug Delivery*, Tracha, P. J. (ed), CRC Press, Boca Raton, Fla., 1991; Lundsted, L. G. and Schmolka, I. R. "The Synthesis and Properties of Block Copolymer Polyol Surfactants", in *Block and Graft Copolymerization*, vol 2, Ceresa, R. J. (ed). John Wiley and Sons, New York, N.Y. 1976). Although composed of the same two monomers, they vary in total molecular weight, polyoxypropylene to polyoxyethylene ratio, and surfactant properties. The poloxamers all have the general structure:

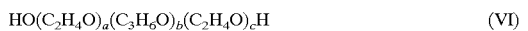

$$HO(C_2H_4O)_a(C_3H_6O)_b(C_2H_4O)_cH \quad (VI)$$

in which a and c are approximately equal, and b is at least 15.

The hydrophobic center block is synthesized in a base catalyzed ether condensation using propylene glycol as the initiator and sequentially adding propylene oxide under an inert, anhydrous atmosphere, at elevated temperature and pressure. Upon reaching the desired molecular weight, the reaction is terminated by neutralization of the catalyst with acid. Using similar reaction conditions, the polymer is then extended by the addition of ethylene oxide to form a hydrophilic segment of polyoxyethylene at each end of the polyoxypropylene block. More than thirty different poloxamers have been synthesized which range in molecular weight from 1,000 to 15,000. The poloxyethylene content of the molecule may vary from 10 to 90% of the weight of the molecule. The poloxamers are freely soluble in water, and are soluble in polar solvents. They are liquids, pastes or solids, depending largely on their polyoxyethylene to polyoxypropylene ratio, and secondarily on their total molecular weight. In general, poloxamers having an average molecular weight of 3,000 or less are liquids if their polyoxyethylene content is not more than 50%. Poloxamers with molecular weights between 3,000 and 5,000 are liquids only if their polyoxyethylene content is 20% or less. Pastes range in molecular weight from 3300 to 6600 with a polyoxyethylene content between 30 and 50%. Solid poloxamers are the largest, having molecular weights of 5,000 to 15,000 and a polyoxyethylene content of 70% or greater.

A nomenclature system has been developed in which each poloxamer has been assigned a number composed of three digits. This number indicates the molecular weight of the hydrophobe and the polyoxyethylene content of the respective poloxamer. The approximate molecular weight of the hydrophobic polyoxypropylene block is obtained by multiplying the first two digits by 100. The approximate weight percent of polyoxyethylene is obtained is multiplying the third digit by 10. For example, poloxamer 188 is composed of a center block of polyoxypropylene having an approximate molecular weight of 1,800, and an ethylene oxide content of approximately 80% of the total molecular weight. Since in Structure VI, a and c are statistically equal, poloxamer 188 should consist of a polyoxypropylene block having a molecular weight of about 1,800, flanked on either end by polyoxyethylene segments with molecular weights of about 3,600. In fact, nominal molecular weights and polyoxyethylene to polyoxypropylene ratios vary among manufacturing lots and among suppliers.

Because the poloxamers are the products of a sequential series of reactions, the molecular weights of individual poloxamer molecules are statistical distributions about the average molecular weight. When poloxamer 407 was analyzed by gel permeation chromatography, a bimodal molecular weight distribution was observed (FIG. 1). The larger peak accounted for approximately 85% of the mass and was composed of molecules having molecular weights between 9,000 and 20,000. A second peak ranging in molecular weight from approximately 4,000 to 8,000 accounted for the remaining 15% of the poloxamer mass. A similar bimodal distribution and broad molecular weight range was observed for poloxamer 188. However, it has been reported that poloxamer 407 obtained from various suppliers have significantly different molecular weight distributions. (Porter, C. J. H., Moghimi, S. M., Davies, M. C., Davis, S. S., and Illum, L., Int. J. Pharm. 83, (1972) 273–276).

The poloxamers are unsaturated to the extent of about 0.02 to 0.07 mEq/g as determined by titration with iodine or mercuric acetate. This unsaturation results from the abstraction of a proton and the formation of an allylic double bond during polyether synthesis. This double bond causes termination of the polymerization process. The unsaturated poloxamer molecules partition overwhelmingly into the lower molecular weight fraction during gel permeation chromatography. This suggests that the broad molecular weight range observed for the commercially available poloxamers is at least in part due to early chain termination. It has been claimed that this termination process can be minimized by using a cesium hydroxide catalyst in place of sodium or potassium hydroxide during polyether synthesis (Ott, R. A., U.S. Pat. No. 4,764,567, 1988).

Because they contain both hydrophilic and hydrophobic regions, poloxamer molecules form micelles in aqueous solution if their polyoxypropylene region is large enough. Their aggregation behavior, however, is quite complex, and cannot be described by simply determining the critical micelle concentration for each polymer. Studies measuring changes in surface-tension with poloxamer concentration indicated two inflection points (Prasad, K. N., Luong, T. T., Florence, A. t., Paris, J., Vaution, C. Seiller, M., and Puisieux, F., J. Colloid Interface Sci., 69, 2, 225–232, 1979). The first inflection point may be due to conformational changes of the individual poloxamer molecules or intermolecular interactions involving a small number of molecules. The second inflection point, at a higher poloxomer concentration, is thought to result from multimolecular aggregation. Zhou, Z., and Chu, B., J. Colloid Interface Sci., 126, 1, 171–180, 1988 observed that as the concentration of poloxamer 188 in an aqueous solution increased, a plot of temperature versus hydrodynamic radius was shifted to the left, indicating an inverse relationship between temperature and critical micelle concentration. Between 40 and 80° C. the aggregation number of the micelles rose sharply. Rassing, J., and Attwood, D., Inter. J. Pharm. 13, 47–55, 1983 studied the aggregation behavior of poloxamer 407 over a temperature range of 10 to 40° C. They concluded from measurements of the radius of gyration, that below 10° C. the polymer exists largely as loosely associated aggregates of extended molecules, and, at least in this temperature range, questioned the presence of coiled monomers as had been previously proposed (Prasad, K. N., Luong, T. T., Florence, A. T., Paris, J., Vaution, C. Seiller, M., and Puisieux, F., J. Colloid Interface Sci., 69, 2, 225–232, 1979). Above 10° C. light scattering measurements indicate that the aggregates become larger and more highly organized, and above approximately 25 ° C., they are spherical entities whose aggregation number increases with increasing temperature. Similar behavior has been reported for poloxarners 184 and 237. It is thus apparent that there are no single values for critical micelle concentration, critical micelle temperature, or aggregation number for the poloxamers.

Table 1 (below) provides viscosities in centipoise of aqueous solutions of poloxamer 407. The abrupt increase in viscosity indicates gelation at a characteristic temperature for each concentration of poloxamer.

TABLE 1

| Temperature °C. | Concentration of poloxamer 407 in water (w/w %) | | | | |
|---|---|---|---|---|---|
| | 18 | 20 | 25 | 28 | 30 |
| 5 | <1000 | <1000 | <1000 | <1000 | <1000 |
| 10 | <1000 | <1000 | <1000 | <1000 | <1000 |
| 15 | <1000 | <1000 | <1000 | 158000 | 254000 |
| 20 | <1000 | <1000 | 214000 | 248000 | 306000 |
| 25 | 76000 | 118000 | 250000 | 268000 | 320000 |
| 30 | 107000 | 138000 | 254000 | 272000 | 334000 |
| 35 | 120000 | 140000 | 258000 | 276000 | 338000 |

Concentrated aqueous solutions of many of the poloxamers form gels in a fully reversible, temperature dependent process. A 20% solution of poloxamer 407 forms a solid gel at 25° C. (Table 1), but other poloxamers act similarly, at higher concentrations. The gelation behavior of the poloxamers is explained by their complex aggregation behavior. Although the polyoxypropylene segment of the poloxamer molecule is hydrophobic, its ether oxygens form hydrogen bonds with water molecules. For this reason, the transfer energy of a propyleneoxide unit from the aqueous to the micellar phase is a fairly low 0.3 kT at 25° C., which results in a loose association of molecules. However, at higher temperatures, the polyoxypropylene segments are dehydrated. This has been shown to occur over a fairly broad temperature range, below the temperature at which gelation occurs. In addition, the aggregation number of the micelles increases with increasing temperature. These two phenomena, loss of water and aggregation of more poloxamer molecules per micelle compensate for each other and the hydrodynamic radius remains approximately constant over a broad temperature range. At higher temperatures, the polyoxyethylene chains begin to dehydrate as well. Upon the loss of water, the polyoxyethylene chains of different micelles interact with each other, if the poloxamer concentration is high enough, and gelation occurs. This process is fully reversible, and if the temperature of a poloxamer gel is reduced, rehydration occurs and the solution returns to the liquid phase.

In practicing this invention, the concentration of poloxamers employed in the formulations are such that the formulation viscosities about 1000 CPS or less. At this viscosity, the formulations remain liquid and exhibit antiadhesion formation activity when applied to tissues.

The poloxamers are widely used in topical and oral consumer products as solubilizers, emulsifiers, stabilizers, dispersing, suspending and coating agents. An extensive amount of research has been done on similar uses of the poloxamers for drug delivery. A monograph setting specifications and analytical methods for poloxamers 124, 188, 237, 338 and 407 has been included in the United States National Formulary since 1990. Poloxamer 188 is included in the British Pharmacopea.

Because their backbone is composed of ether linkages, none of the poloxamers is known to be metabolized in the body. They are generally nonirritating and do not cause sensitization when applied topically. The oral $LD_{50}$ values for the liquid poloxamers are generally greater than 1 gm/km of body weight, and for solids and pastes greater than 10 gm/km. Two of the poloxamers, 188 and 407, have been studied extensively for internal medical use.

The following examples illustrate the various aspects of the invention but are not intended to limit its scope. Where not otherwise specified throughout this specification and claims, temperatures are given in degrees centigrade, and parts, percentages, and proportions are by weight.

EXAMPLE 1

An aqueous solution was made of a polyoxyethylene-polyoxypropylene block copolymer having the structure generically shown as formula IV and having a polyoxypropylene hydrophobe base average molecular weight of about 4000, a total average molecular weight of about 11,500, and containing oxyethylene groups in the amount of at least about 70% by weight of the total weight of copolymer. This copolymer is sold under the trademark PLURONIC® F-127 by the BASF Corporation, Parsippany, N.J. (also known as Poloxamer 407). A solution was made by dissolving said polymer in cold (4° C.) distilled water to give a concentration of 30% by weight in accordance with the cold process described above for forming aqueous solutions. More specific solution procedures are described in "Artificial Skin I Preparation and Properties of Pluronic F-127 Gels for Treatment of Burns", *J. Biomed. Mater. Res.* 6, 527, 1972, incorporated herein by reference. The block copolymer has the formula:

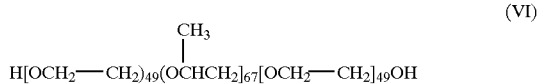

(VI)

This solution is a liquid at 4° C. and is non-gelling but is adherent to living tissue upon contact. It is mixed into the following formula:

1A

| INGREDIENT | PERCENT BY WEIGHT |
| --- | --- |
| Poloxamer 407, NF | 14.00 |
| Tromethamine (TRIS), USP | 0.1091 |
| Maleic Acid | 0.1045 |
| Sodium Hydroxide pellets, USP | 0.0420 |
| Sodium chloride, USP | 0.160 |
| Sterile Water for Irrigation, USP | 85.584 |

First, the water was weighed in a tared vessel. Second, the tromethamine, maleic acid and sodium hydroxide were added to the water and mixed for twenty minutes. The pH and osmolality of the solution were tested. The solution was cooled to 10° C. and the poloxamer was added to the solution over a two hour period with constant stirring. The solution was stored under a nitrogen atmosphere at 4° C. for fifteen hours to effect a reduction in the foam content of the solution. The solution was tested for pH, osmolality, and viscosity and the results were 7.0–7.8, 280–320 mOsm/kg and 1,000 centipoise at temperature range of 2 to 35° C., respectively. The solution was packaged into 30 cc serum vials, capped with rubber stoppers and sterilized with steam at 121° C. and 15 psi for twenty minutes. Each vial was cooled to 4° C. and mixed for ten minutes to ensure uniform solution.

EXAMPLE 2

The following formulation was prepared by following the steps defined in Example 1.

2A

| DESCRIPTION | % (w/w) | UNIT | EXAMPLE |
| --- | --- | --- | --- |
| Poloxamer 188, NF | 16.00 | gm | 16.00 |
| Tromethamine (TRIS), USP | 0.1091 | gm | 0.11 |
| Maleic Acid | 0.1045 | gm | 0.10 |
| Sodium Hydroxide pellets, USP | 0.0420 | gm | 0.04 |
| Sterile Water For Irrigation, USP | 83.744 | gm | 83.74 |

First, the water was weighed in a tared vessel. Second, the tromethamine, maleic acid and sodium hydroxide were added to the water and mixed for twenty minutes. The pH and osmolality of the solution were tested. The solution was cooled to 10° C. and the poloxamer was added to the solution over a two hour period with constant stirring. The solution was stored under a nitrogen atmosphere at 4° C. for fifteen hours to effect a reduction in the foam content of the solution. The solution was tested for pH, osmolality, and viscosity and the results were 320 mOsm/kg and >1000 centipoise at temperature range of 25° C. to 35° C., respectively. The solution was packaged into 30 cc serum vials, capped with rubber stoppers and sterilized with steam at 121° C. and 15 psi for twenty minutes. Each vial was cooled to 4° C. and mixed for ten minutes to ensure uniform solution.

EXAMPLE 3

Analytical Method

Measurement of Pentoxifylline Release from Various Formulations

Approximately 15 cm of SpectraPor regenerated cellulose dialysis tubing (6000–8000 molecular weight cut off, cat. # 132650, Source: Spectrum Medical Industries, Inc.) is rinsed in distilled water to remove preservatives. One end is sealed with the appropriate sized closure.

5 ml of the formulation to be tested was placed in the tubing and the other end sealed as close as possible to the sample. The tubing is placed in a beaker containing 95 ml of phosphate buffer (0.05 M $KH_2PO_4$+0.0391 M NaOH, pH 7.4) and a magnetic stirring bar. The solution was mixed on low speed at room temperature. One ml samples were withdrawn (via pipet) at each time point and diluted to an appropriate volume (either 10 or 25 ml) with water for UV absorbance measurements.

UV absorbance of the test solution is determined at 273 nm versus a water blank. A 100% release standard is prepared by diluting 5 ml of the formulation to be tested to 100 ml with phosphate buffer. 1 ml of this solution is then diluted to 25 ml with water for absorbance measurement.

Percent released is calculated by ratioing the absorbance of the test solution at each time point against the 100% release standard, taking into account any differences in dilution, the small decrease in volume of the test solution at each time point caused by earlier sample withdrawals and the amount of pentoxifylline already removed due to previous samplings.

Figure 2:
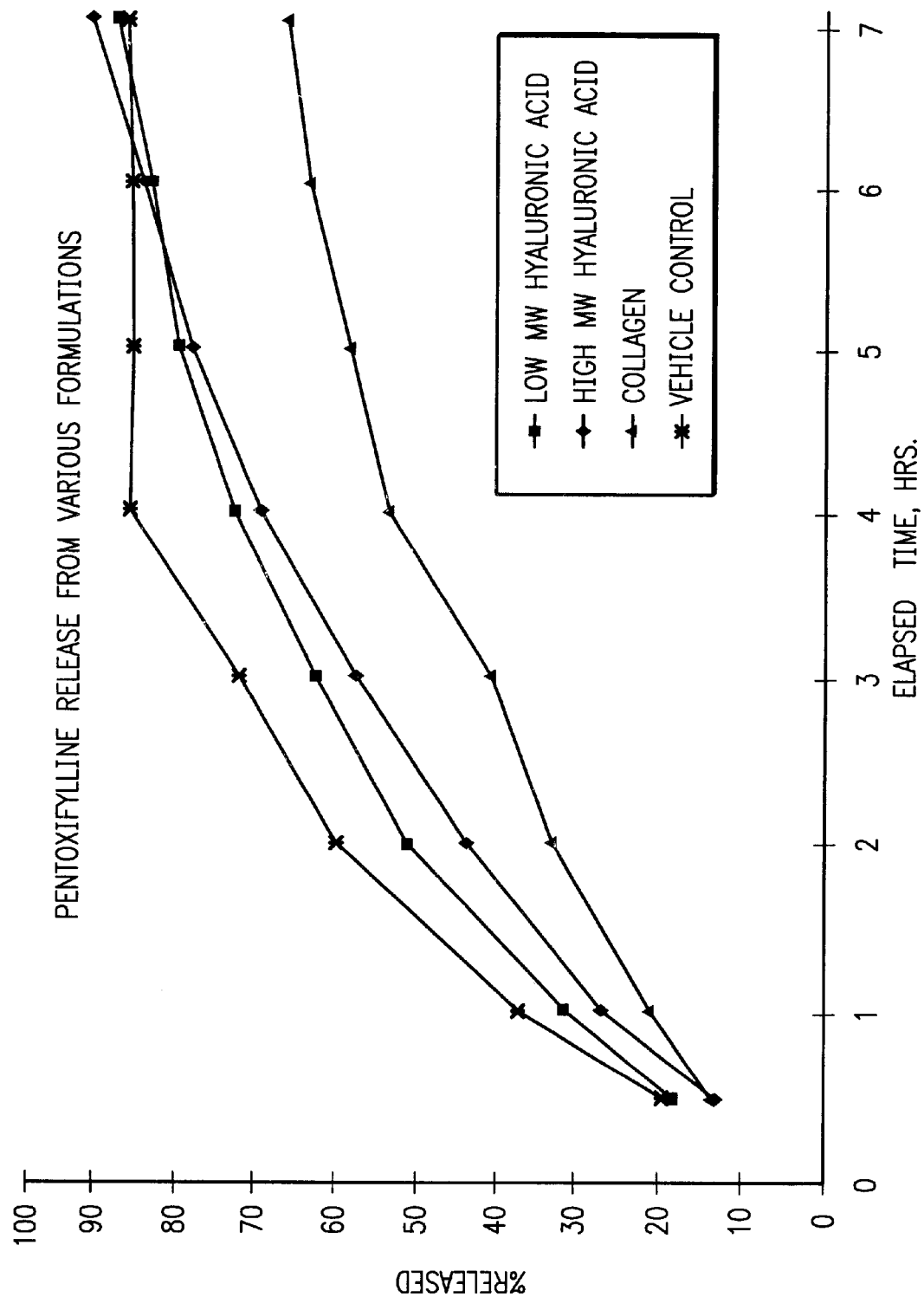
FIG. 2 illustrates pentoxifylline release from formulations of carboxymethylcellulose, hydroxyethylcellulose, sodium alginate, xanthan gum, and phosphate buffer (vehicle control).
Figure 3:
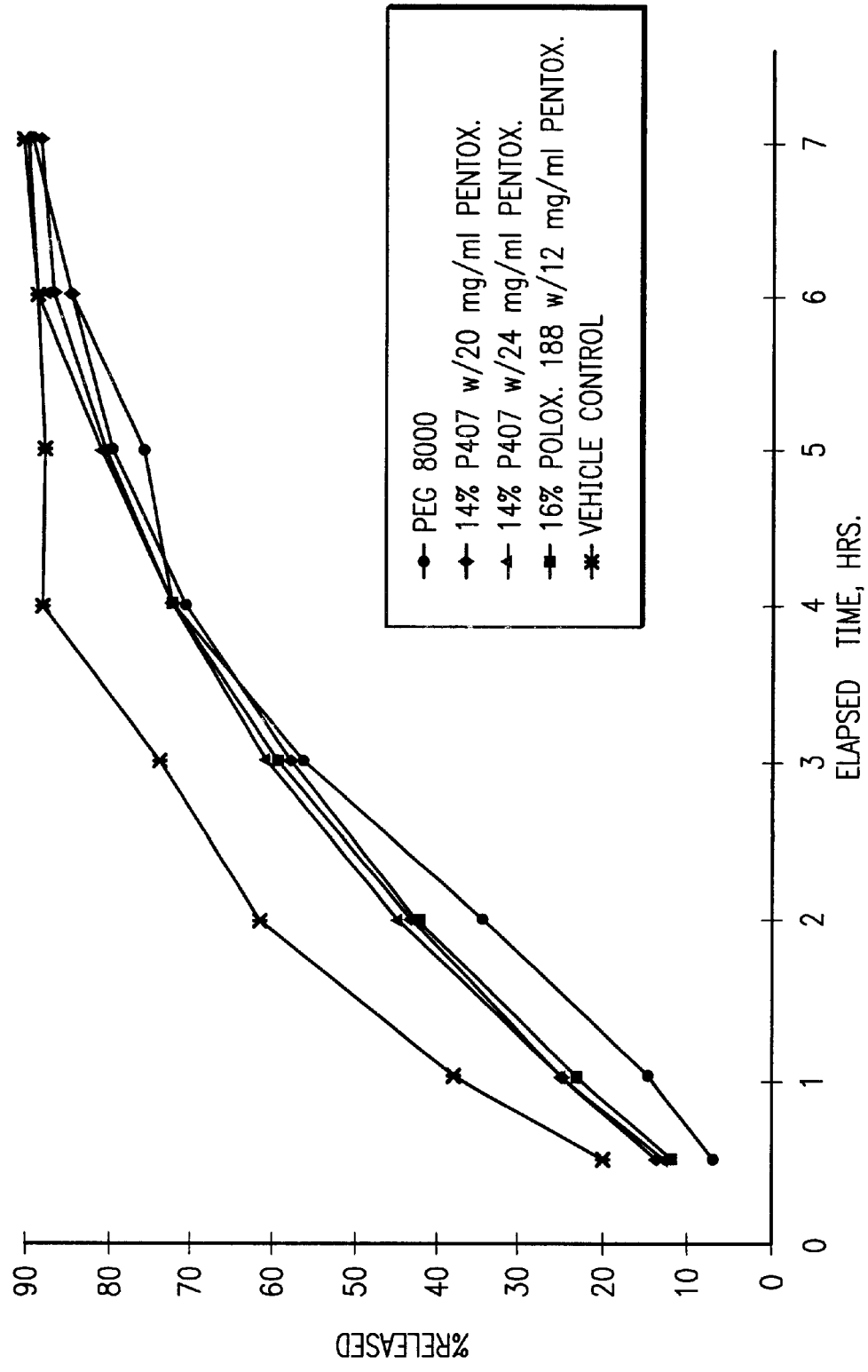
FIG. 3 illustrates pentoxifylline release from formulations of low MW hyaluronic acid, high MW hyaluronic acid, collagen, and phosphate buffer (vehicle control).
Figure 4:
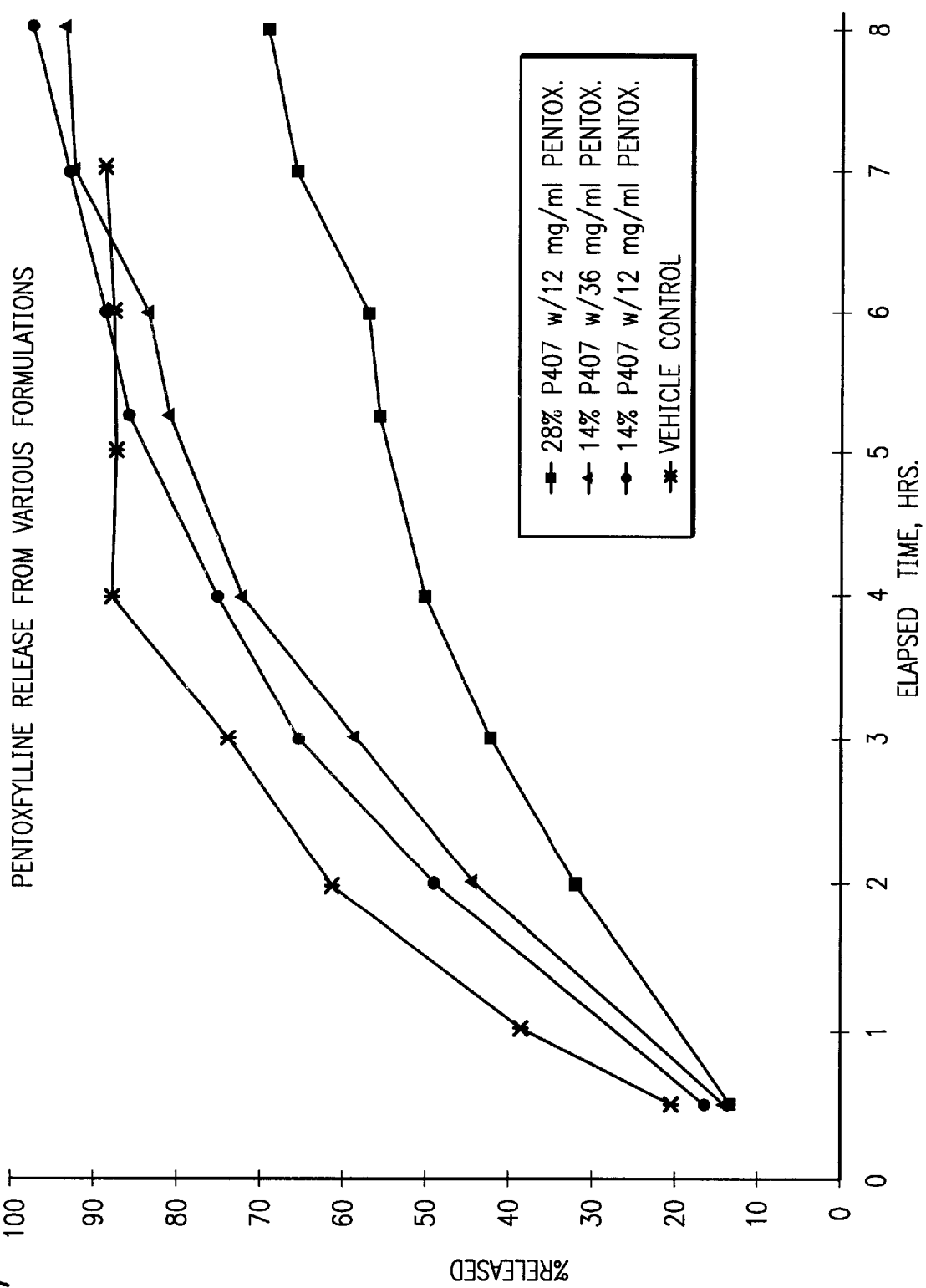
FIG. 4 illustrates pentoxifylline release formulations from PEG 8000, 14% poloxamer 407 with 20 mg/ml pentoxifylline, PEG 8000, 14% poloxamer 407 with 20 mg/ml pentoxifylline, 14% poloxamer 407 with 24 mg/ml pentoxifylline, and 16% poloxamer 188 with 12 mg/ml pentoxifylline, and phosphate buffer (vehicle control).

The results are summarized in FIGS. 1–5. FIG. 1 is a chromogram of a poloxamer 407 analysis by gel permeation choromography. FIG. 2 illustrates pentoxifylline release from formulations of carboxymethylcellulose, hydroxyethylceuulose, sodium alginate, xanthan gum, and phosphate buffer (vehicle control). FIG. 3 illustrates pentoxifylline release from formulations of low MW hyaluronic acid, high MW hyaluronic acid, collagen, and phosphate buffer (vehicle control). FIG. 4 illustrates pentoxifylline release formulations from PEG 8000, 14% poloxamer 407 with 20 mg/ml pentoxifylline, PEG 8000, 14% poloxamer 407 with 20 mg/ml pentoxifylline, 14% poloxamer 407 with 24 mg/ml pentoxifylline, and 16% poloxamer 188 with 12 mg/ml pentoxifylline, and phosphate buffer (vehicle control). FIG. 5 illustrates pentoxifylline release from formulations of 28% poloxamer 407 with 12 mg/ml pentoxifylline, 14% poloxamer 407 with 36 mg/ml pentoxifylline and 14% poloxamer 407 with 12 mg/ml penoxifylline.

| Representative Formulations | | |
|---|---|---|
| Ingredient | Source | Weight % |
| *Formulation: Sodium Alginate Gel with Pentoxifylline* | | |
| Sodium Alginate | TIC Gums | 2.000 |
| Pentoxifylline | ICN | 1.200 |
| Tromethamine USP | Spectrum | 0.109 |
| Maleic Acid | Spectrum | 0.105 |
| Sodium Hydroxide, USP | Spectrum | 0.042 |
| Purified Water | Bamsted | 96.544 |
| *Formulation: Collagen Gel with Pentoxifylline* | | |
| Hydracol Soluble Collagen | Gattefasse | 1.000 |
| Pentoxifylline | ICN | 1.200 |
| Tromethamine USP | Spectrum | 0.109 |
| Maleic Acid | Spectrum | 0.105 |
| Sodium Hydroxide, USP | Spectrum | 0.042 |
| Purified Water | Bamsted | 97.540 |
| *Formulation: Vehicle Control with Pentoxifylline* | | |
| Pentoxifylline | ICN | 1.200 |
| Tromethamine USP | Spectrum | 0.109 |
| Maleic Acid | Spectrum | 0.105 |
| Sodium Hydroxide, USP | Spectrum | 0.042 |
| Sodium Chloride | Spectrum | 0.750 |
| Purified Water | Bamsted | 97.794 |
| *Formula: PEG 8000 with Pentoxifylline* | | |
| PEG 8000 | Union Carbide | 10.000 |
| Pentoxifylline | ICN | 1.200 |
| Tromethamine USP | Spectrum | 0.109 |
| Maleic Acid | Spectrum | 0.105 |
| Sodium Hydroxide, USP | Spectrum | 0.042 |
| Purified Water | Bamsted | 88.544 |
| *Formula: 14% Poloxamer 407 with 20 mg/ml Pentoxifylline* | | |
| Poloxamer 407 | BASF | 14.000 |
| Pentoxifylline | ICN | 2.000 |
| Tromethamine USP | Spectrum | 0.109 |
| Maleic Acid | Spectrum | 0.105 |
| Sodium Hydroxide, USP | Spectrum | 0.042 |
| Sodium Chloride | Spectrum | 0.040 |
| Purified Water | Bamsted | 83.700 |
| *Formula: 14% Poloxamer 407 with 24 mg/ml Pentoxifylline* | | |
| Poloxamer 407 | BASF | 14.000 |
| Pentoxifylline | ICN | 2.400 |
| Tromethamine USP | Spectrum | 0.109 |
| Maleic Acid | Spectrum | 0.105 |
| Sodium Hydroxide, USP | Spectrum | 0.042 |
| Sodium Chloride | Spectrum | 0.020 |
| Purified Water | Bamsted | 83.324 |
| *Formula: 16% Poloxamer 188 with 12 mg/ml Pentoxifylline* | | |
| Poloxamer 188 | BASF | 16.000 |
| Pentoxifylline | ICN | 1.200 |
| Tromethamine USP | Spectrum | 0.109 |
| Maleic Acid | Spectrum | 0.105 |
| Sodium Hydroxide, USP | Spectrum | 0.042 |
| Purified Water | Bamsted | 82.544 |
| *Formula: 28% Poloxamer 407 with 12 mg/ml Pentoxifylline* | | |
| Poloxamer 407 | BASF | 28.00 |
| Pentoxifylline | ICN | 1.20 |
| Tromethamine, USP | Spectrum | 0.109 |
| Maleic Acid | Spectrum | 0.105 |
| Sodium Hydroxide, USP | Spectrum | 0.042 |
| Purified Water | Bamsted | 70.544 |
| *Formula: 14% Poloxamer 407 with 36 mg/ml Pentoxifylline* | | |
| Poloxamer 407 | BASF | 14.00 |
| Pentoxifylline | ICN | 3.60 |
| Tromethamine, USP | Spectrum | 0.109 |
| Maleic Acid | Spectrum | 0.105 |
| Sodium Hydroxide, USP | Spectrum | 0.042 |
| Purified Water | Bamsted | 82.144 |
| *Formula: 14% Poloxamer 407 with 12 mg/ml Pentoxifylline* | | |
| Poloxamer 407 | BASF | 14.00 |
| Pentoxifylline | ICN | 1.20 |
| Tromethamine, USP | Spectrum | 0.109 |
| Maleic Acid | Spectrum | 0.105 |
| Sodium Hydroxide, USP | Spectrum | 0.042 |
| Sodium Chloride | Spectrum | 0.040 |
| Purified Water | Bamsted | 84.504 |

EXAMPLE 4

Surgical Trial on Prospective Study on Adhesions in the Rabbit Model

To assess the potential of poloxamer 407 with pentoxifylline to prevent or reduce adhesions the following experiment was performed.

Preparation of 14% poloxamer 407 with 1.2% pentoxifylline solution.

| INGREDIENT | PERCENT BY WEIGHT |
|---|---|
| Poloxamer 407, NF | 14.00 |
| Pentoxifylline | 1.20 |
| Tromethamine (TRIS), USP | 0.1091 |
| Maleic Acid | 0.1045 |
| Sodium Hydroxide pellets, USP | 0.0420 |
| Sodium Chloride, USP | 0.04 |
| Sterile Water for Irrigation, USP | 82.54 |

Water was weighed into a tared vessel. Pentoxifylline, tromethamine, maleic acid and sodium hydroxide were added to the water and mixed for twenty minutes. The pH and osmolality of the solution were tested and found to be 7.6 and 109 mOsm/Kg, respectively. The solution was cooled to 6° C. and the poloxamer was added to the solution over a two hour period with constant stirring. The solution was stored under a nitrogen atmosphere at 4° C. for fifteen hours to effect a reduction in the foam content of the solution. The solution was tested for pH and osmolality and the results were 7.4 and 290 mOsm/Kg, respectively. The solution was packaged into 30 cc serum vials, capped with rubber stoppers and sterilized with steam at 121° C. and 15 psi for twenty minutes. The vials were cooled to 4° C. and swirled for ten minutes to ensure uniform distribution.

The experiment utilized eighteen, healthy, female, New Zealand White rabbits. The uterine horn was exteriorized then abraded by scraping 20–30 times with a no. 10 scalpel blade until a wound was produced that had punctate bleeding. Nine of the rabbits received 3.0 ml of 14% poloxamer 407 with 1.2% pentoxifylline delivered at 0° C. Five rabbits received a physiologic buffer also delivered at 0° C. Four rabbits received no treatment. The opposite uterine horn was untreated. The uterine horns were returned to the peritoneal cavity and the incision was closed. On the 12th day after the initial surgery, the animals were necropsied and the adhesions were scored. The adhesions were scored as follows: 0=no adhesions, 1=adhesions up to 25% of area, 2=adhesions from 25% to 50% of area, 3=greater than 50% of area, 4=100% adhesions.

| Treatment | Adhesion Score (Mean) |
| --- | --- |
| 14% poloxamer 407 with 12% pentoxifylline | 0.67 |
| physiologic buffer | 2.4 |
| no treatment | 2.35 |

Preparation of poloxamer 188 solution

| Ingredient | Percent by Weight |
| --- | --- |
| Poloxamer 188, NF | 16.00 |
| Pentoxifylline | 1.20 |
| Tromethamine (TRIS), USP | 0.1091 |
| Maleic Acid | 0.1045 |
| Sodium Hydroxide pellets, USP | 0.0420 |
| Sterile Water For Irrigation, USP | 82.54 |

Water was weighed into a tared vessel. Pentoxifylline, tromethamine, maleic acid and sodium hydroxide were added to the water and mixed for twenty minutes. The pH and osmolality of the solution were tested and found to be 7.7 and 50 mOsm/Kg, respectively. The solution was cooled to 6° C. and the poloxamer was added to the solution over a two hour period with constant stirring. The solution was stored under a nitrogen atmosphere at 4° C. for fifteen hours to effect a reduction in the foam content of the solution. The solution was tested for pH and osmolality and the rabbits were 7.4 and 140 mOsm/Kg, respectively. The solution was packaged into 30 cc serum vials, capped with rubber stoppers and sterilized with steam at 121° C. and 15 psi for twenty minutes. The vials were cooled to 4° C. and swirled for ten minutes to ensure uniform distribution of pentoxifylline in the vial.

What we claim:

1. A method of inhibiting the formation/reformation of internal adhesions which comprises administering to the tissues of a mammal an aqueous non-gelling composition comprising:
    about 65%–95% by weight of water,
    about 5% to 35% by weight of a polyoxyalkylene block polymer of the formula:

$$Y[(A)_n\text{—E—H}]_x$$

wherein A is a polyoxyalkylene moiety having an oxygen/carbon atom ratio of less than approximately 0.5, x is at least 1, Y is derived from water or an organic compound containing x reactive hydrogen atoms, E is a polyoxyethylene moiety, n has a value such that such that the minimum molecular weight of A is between about 500 to about 900, as determined by the hydroxyl number of an intermediate of the formula:

$$Y[(A)\text{—H}]_x$$

and the total molecular weight of the polyoxyalkylene block copolymer is at least about 5000.

2. The method of claim 1, wherein Y is derived from a water soluble organic compound having from 1 to about 6 carbon atoms.

3. The method of claim 2, wherein the polyoxyalkylene block copolymer is selected from the group consisting of: a polyoxyethylene-polyoxybutylene block copolymer; and, a polyoxyethylene-polyoxypropylene block copolymer and mixtures thereof, and, the polyoxyethylene-polyoxypropylene moiety constitutes at least about 70% by weight of the polyoxyalkyelene block copolymer.

4. The method of claim 1 wherein the pH of the aqueous composition is maintained at about 7.4+/−0.4.

5. The method of claim of claim 4 wherein the polyoxyalkylene block polymer is selected from block copololymers which form aqueous solutions at a concentration of about 7% to about 16% by weight of the total weight of the composition.

6. The method of claim 1 wherein Y is a compound selected from the group consisting of propylene glycol, butylene glycol, glycerine, pentaerythritol, trymethylopropane, ethylenediamine and mixtures thereof.

7. The method of claim 1 wherein the aqueous composition is a hyper-, iso- or hypo-osmotic to mammalian body tissues.

8. The method of claim 1, wherein the aqueous composition further comprises an effective amount of pentoxyfylene.

* * * * *